(12) United States Patent
Giamanco et al.

(10) Patent No.: US 6,206,862 B1
(45) Date of Patent: Mar. 27, 2001

(54) SHOWER DOUCHING SYSTEM

(76) Inventors: Joseph A. Giamanco, 8225 Bluff Creek Ave., Las Vegas, NV (US) 89128; Roger D. Raines, 6201 Boulder Hwy, Space 143, Las Vegas, NV (US) 89122

( * ) Notice: Subject to any disclaimer, the term of this patent is extended or adjusted under 35 U.S.C. 154(b) by 0 days.

(21) Appl. No.: 09/303,628

(22) Filed: May 3, 1999

(51) Int. Cl.$^7$ .................................................. A61M 31/00
(52) U.S. Cl. ............................................................ 604/279
(58) Field of Search .................................... 604/275, 279, 604/39, 212, 514–515, 517; 607/81–82, 84

(56) References Cited

U.S. PATENT DOCUMENTS

| | | |
|---|---|---|
| 3,921,635 | 11/1975 | Gauthier . |
| 4,601,709 | 7/1986 | Kabbaby . |
| 4,642,100 | 2/1987 | Kabbaby . |
| 4,911,704 * | 3/1990 | Dixon ...................................... 604/83 |
| 5,102,387 | 4/1992 | Jorde . |
| 5,241,714 * | 9/1993 | Barry ........................................ 4/605 |
| 5,304,116 * | 4/1994 | Cornelius ............................... 604/39 |

* cited by examiner

*Primary Examiner*—Sharon Kennedy
*Assistant Examiner*—Catherine Serke
(74) *Attorney, Agent, or Firm*—Harry M. Weiss; Jeffrey Weiss; Weiss & Moy, P.C.

(57) ABSTRACT

A shower douching system is shown. The shower douching system comprises; a solution reservoir, a shower passageway coupled to the solution reservoir, and a controllable shower douche coupled to the shower passageway and coupled to the solution reservoir for controlling a shower fluid flow diversion. The controllable shower douche comprises a valve coupled to a shower bypass channel for controlling the shower fluid flow diversion, and further comprises an eductor connected downstream of the shower bypass channel for creating a low pressure condition within the eductor. The eductor is coupled to a solution suction channel extending substantially within the solution reservoir, and a douche fluid outlet channel is coupled to the valve.

4 Claims, 1 Drawing Sheet

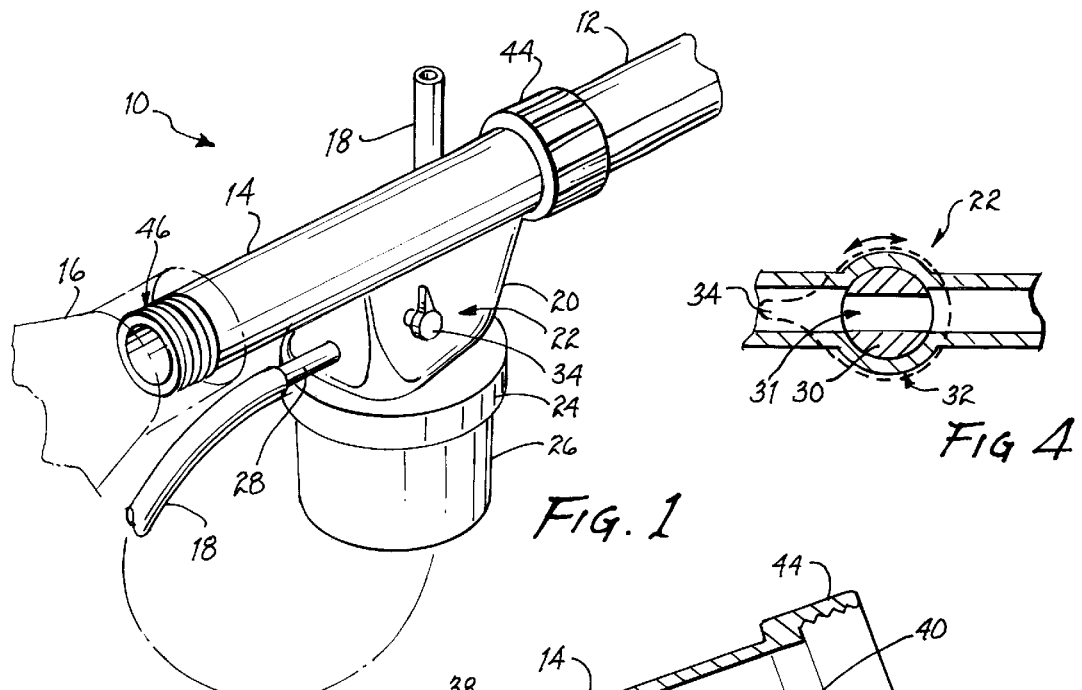
FIG. 1
FIG. 4
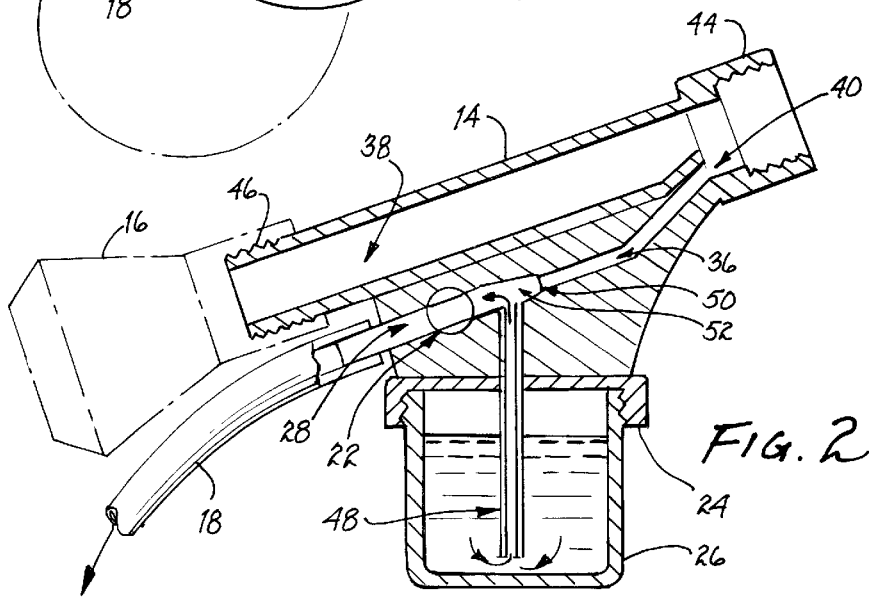
FIG. 2
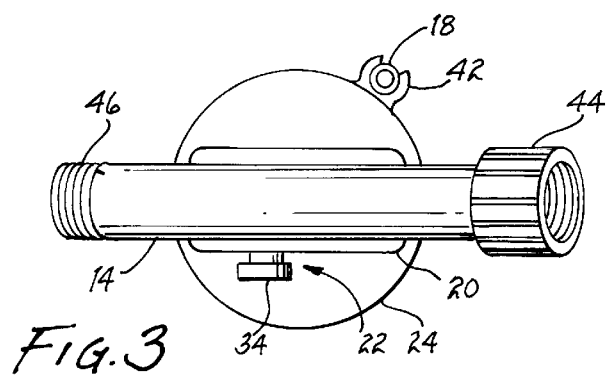
FIG. 3

US 6,206,862 B1

SHOWER DOUCHING SYSTEM

FIELD OF THE INVENTION

This invention is in the field of Personal Hygiene Systems, and more particularly is a douching system that has the features of allowing continuous shower operation while also allowing controllable douching.

DESCRIPTION OF THE RELATED ART

In the field of Personal Hygiene Systems, many different douching devices are available on the market. These devices typically consist of either a stand-alone device, or a shower attachment device for use in a shower. The typical shower attachment device is used by attaching a douche device in place of, or over, a shower nozzle and then diverting the water flow through the douching device. Examples of these douching devices include those such as described in U.S. Pat. No. 4,642,100 by Kabbaby, in which the full water flow is diverted from showering to douching, or such as the device in U.S. Pat. No. 5,102,387 by Jorde which attaches over the shower nozzle thus using the entire shower water flow for douching. While these types of douche devices do work, they have many drawbacks however. The diversion of the entire shower water flow through the douching device prevents the user from easily controlling the pressure or volume of the douching flow. Furthermore, the diversion of the entire shower water flow through the douching device prevents the user from easily controlling the water temperature from the douching device. Additionally, the diversion of the entire shower water flow prevents simultaneously showering while douching.

Therefore, a need existed for a system of easily controlling the pressure or volume of the douching flow. A further need existed for a system of easily controlling the water temperature from the douching device. Yet a further need existed for a system that will allow simultaneous showering and douching.

SUMMARY OF THE INVENTION

An object of the present invention is to provide a system for easily controlling the pressure or volume of the douching flow.

A further object of the present invention is to provide a system for easily controlling the water temperature from the douching unit.

Yet another object of the present invention is to provide for a system that allows simultaneous showering and douching.

BRIEF DESCRIPTION OF THE PREFERRED EMBODIMENTS

In a preferred embodiment of the present invention, a shower douching system is disclosed. The shower douching system comprises: a solution reservoir, a hollow passageway coupled to the solution reservoir, and a controllable shower douche coupled to the solution reservoir.

In another embodiment of the present invention, a shower douching system is disclosed. The shower douching system comprises: a solution reservoir, a shower passageway coupled to the solution reservoir, and a controllable shower douche coupled to the shower passageway and coupled to the solution reservoir for controlling a shower fluid flow diversion. The controllable shower douche comprises a valve coupled to a shower bypass channel for controlling the shower fluid flow diversion, and further comprises an eductor connected downstream of the shower bypass channel for creating a low pressure condition within the eductor. The eductor is coupled to a solution suction channel extending substantially within the solution reservoir, and a douche fluid outlet channel is coupled to the valve.

BRIEF DESCRIPTION OF THE DRAWINGS

FIG. 1 is an elevated perspective view of the shower douching system of the present invention.

FIG. 2 is a cross-sectional view showing the internal arrangement features of the shower douching system of the present invention.

FIG. 3 is a top view of the shower douching system of the present invention.

FIG. 4 is a cross-sectional view of the douche control valve assembly of the shower douching system of the present invention.

DESCRIPTION OF THE PREFERRED EMBODIMENTS

Referring to FIG. 1, an elevated perspective view of the shower douching system of the present invention is shown ("the system 10" hereinafter.) The system 10 is constructed and adapted to be coupled to a plumbing nipple 12 as is conventionally located in a shower or tub installation. Normally, a shower's plumbing nipple 12 will have a shower nozzle 16 directly connected to it. The shower nozzle 16 is removed and the system 10 coupled in its place. It will be understood by those skilled in the art that the use of the term shower is not limiting herein as the system 10 may also be coupled to a different plumbing nipple such as a plumbing nipple coupled to and used with a tub faucet (not shown herein). It will be further understood that the scope and function of the shower douching system 10 of the present invention will not be detrimentally described or limited by such usage of the present invention with a tub faucet, or other water sources.

The system 10 comprises a coupling 44 rotatably connected to the shower water extension tube 14. The coupling 44 connects the system 10 to the plumbing nipple 12 by screwing onto the shower plumbing nipple 12. This coupling thereby connects the shower water extension tube 14 of the system 10 to the plumbing nipple 12. The shower nozzle 16, previously removed, is connected to the shower water extension tube 14 by screwing the shower nozzle 16 onto the shower nozzle coupling 46.

The system 10 is further comprised of the main douche body 20. The main douche body 20 comprises the solution reservoir coupling flange 24 to which the solution reservoir 26 is connected. Protruding from the main douche body 20, located generally proximate to and beneath the shower nozzle coupling 46 is the discharge tube 28. As will be explained in more detail further on, the discharge tube 28 extends into the main douche body 20. Connected to the discharge tube 28 is the douche flexible tubing 18. Located within and extending from the side of the main douche body 20 is the douche control valve assembly 22, of which the douche control valve operator 34 is shown pointing upwardly thus indicating that the douche control valve assembly 22 is in the off, or non-douche flow, position.

Referring now to FIG. 2, a cross-sectional view showing the internal arrangement features of the shower douching system 10 of the present invention is shown. As shown therein, the shower water extension tube 14 comprises a shower nozzle water channel 38 that allows the continuous flow of water from the plumbing nipple 12 (see FIG. 1) to and through the shower nozzle 16. Located just downstream of the coupling 44 is the eductor water supply channel inlet 40. The eductor water supply channel inlet 40 is connected to the eductor water supply channel 36, which is in turn connected to the eductor venturi nozzle 50, and thence to the eductor mixing chamber 52. Coupled to the eductor mixing chamber 52 is the douche control valve assembly 22, to which is coupled the discharge tube 28. Coupled to the discharge tube 28 is the douche flexible tubing 18. Further coupled to the eductor mixing chamber 52 is the solution reservoir eductor suction tube 48, which extends down into the solution reservoir 26.

Referring to FIG. 4, a cross-sectional view of the douche control valve assembly 22 of the shower douching system 10 of the present invention is shown. The douche control valve assembly 22, in a preferred embodiment, is a ball type valve assembly. However, other types of valves, well known in the art, may be utilized herein without affecting the scope or operation of the present invention. Referring to FIG. 4, it is shown that the douche control valve assembly 22 comprises a ball 30 within a valve body 32. The ball 30 has a ball channel 31 through the center of the ball 30. The ball 30 is coupled to and rotated by the douche control valve operator 34. If the douche control valve operator 34 is aligned substantially horizontal, or parallel to the shower water extension tube 14, this is the on, or douche flow position, and fluid flow will freely occur through the ball channel 31 of the ball 30. Conversely, if the douche control valve operator 34 is aligned substantially vertical, or perpendicular to the shower water extension tube 14, this is the off, or non-douche flow position, and fluid flow through the douche control valve assembly 22 will be blocked by the side of the ball 30.

Referring to FIG. 3, a top view of the shower douching system 10 of the present invention is shown. In a preferred embodiment the system 10 will further comprise a douche flexible tubing storage clamp 42 coupled to the solution reservoir coupling flange 24. The douche flexible tubing storage clamp 42 is sized and adapted to allow the douche flexible tubing 18 to be securely held and stored by the douche flexible tubing storage clamp 42 when not in use or as desired.

Douche Operation

To operate the system 10, the user will prepare the desired douche solution (details not shown herein) according to personal preference, and place this douche solution into the solution reservoir 26. The solution reservoir 26 is in turn screwed into the solution reservoir coupling flange 24. The douche control valve operator 34 is checked, or positioned to the off, or non-douche flow, position. Once the solution reservoir 26 is securely seated into the solution reservoir coupling flange 24, and the douche control valve operator 34 is in the off position, the shower, or tub, water flow and temperature is adjusted by the user, (details not shown herein). The water flow path for showering is from the plumbing nipple 12 via the shower water extension tube 14, and out the shower nozzle 16.

When the user is ready to commence douching, the user rotates the douche control valve operator 34 to the on, or douche flow, position. The eductor water supply channel inlet 40 will then divert a portion of the water flow that is being supplied from the plumbing nipple 12 (see FIG. 1). The diverted water flow is channeled through the eductor water supply channel 36, to and through the eductor venturi nozzle 50. The water flow through the eductor venturi nozzle 50 into the eductor mixing chamber 52 will result in a low pressure condition with the eductor mixing chamber 52 due to the venturi effect of the eductor venturi nozzle 50. The low pressure within the eductor mixing chamber 52 will cause the douching solution within the solution reservoir 26 to be drawn up through the solution reservoir eductor suction tube 48. The douching solution will be drawn into the eductor mixing chamber 52 where it will become entrained by the shower water flow through the eductor mixing chamber 52. The combined douching solution and shower water flow will pass out of the eductor mixing chamber 52, through the ball channel 31 of the ball 30, and thence through the discharge tube 28. The combined douching solution and shower water flow will next pass through the douche flexible tubing 18 to the user's nozzle (not shown herein.) Throughout the entire time frame from pre-douching, through douching, and after douching the shower water flow is in operation through the system 10, and out the shower nozzle 16. This functionality allows the healthful uninterrupted cleansing of showering before, during, and after douching.

Therefore, throughout the use of a preferred embodiment of the system 10 of the present invention, the shower flow will be easily controlled thus supplying a substantially constant pressure and volume of both the shower flow and the douching flow. Furthermore, the water temperature through the system 10 will remain substantially constant. And finally, a preferred embodiment of the present invention will allow simultaneous showering and douching by the user.

Although the invention has been particularly shown and described with reference to a preferred embodiment thereof, it will be understood by those skilled in the art that changes in form and detail may be made therein without departing from the spirit and scope of the invention.

What is claimed is:

1. A combination shower and douching system comprising, in combination;

a shower head;

a water line connected to said shower head, said water line having an opening therein diverting away a portion of water in said water line;

a solution reservoir having a fluid therein for douching;

a first conduit having a first end connected to said opening in said water line and coupled to said solution reservoir;

a second conduit connected at one end to said first conduit and having the other end located in said fluid within said solution reservoir;

a single valve located in said first conduit downstream of where said one end of said second conduit connects to said first conduit; and venturi means located in said first conduit for enabling said fluid in said solution reservoir to flow up said second conduit and down said first conduit towards a second end thereof when said single valve is in an open position.

2. The system of claim 1 wherein said single valve is a ball type valve.

3. The system of claim 2 wherein an external valve operator is connected to selectively open and close said ball type valve.

4. The system of claim 1 wherein said douching system is a female douching system.

\* \* \* \* \*